United States Patent
Fischbacher

(10) Patent No.: US 9,189,752 B2
(45) Date of Patent: Nov. 17, 2015

(54) INTERPOLATING ISOTONIC REGRESSION FOR BINARY CLASSIFICATION OF SPAM, EXPLICIT MATERIAL OR MALWARE USING INTERPOLATION BASED ON A DELAUNAY TRIANGULATION

(71) Applicant: Google Inc., Mountain View, CA (US)

(72) Inventor: Thomas Fischbacher, Zurich (CH)

(73) Assignee: Google Inc., Mountain View, CA (US)

( * ) Notice: Subject to any disclaimer, the term of this patent is extended or adjusted under 35 U.S.C. 154(b) by 201 days.

(21) Appl. No.: 14/143,192

(22) Filed: Dec. 30, 2013

(65) Prior Publication Data

US 2015/0186796 A1    Jul. 2, 2015

(51) Int. Cl.
*G06F 15/18*   (2006.01)
*G06N 99/00*   (2010.01)
*G06F 19/24*   (2011.01)

(52) U.S. Cl.
CPC .............. *G06N 99/005* (2013.01); *G06F 19/24* (2013.01)

(58) Field of Classification Search
CPC .............................. G06K 9/0021; G06F 19/24
USPC ................................................ 706/12, 45, 62
See application file for complete search history.

(56) References Cited

U.S. PATENT DOCUMENTS

2008/0033672 A1 * 2/2008 Gulati ................... G06N 99/002
                                                               702/69

OTHER PUBLICATIONS

Ozertem et al., Locally Defined Principal Curves and Surfaces, 2011, Journal of Machine Learning Research 12 {2011) 241-274.*
Baraldi et al., Soft_to_hard model transition in clustering_a review, 1999, International Computer Science Institute, pp. 1-21.*
Nielson, Pattern Learning and Recognition on Statistical Manifolds: An Information-Geometric Review, Jul. 2013, Springer-Verlag Berlin Heidelberg, pp. 1-25.*
Kalai et al., The Isotron Algorithm: High-Dimensional Isotonic Regression, 2009, COLT, pp. 1-9.*
Nielson, Pattern Learning and Recognition on Statistical Manifolds: An Information-Geometric Review, Jul. 2013, Springer-Verlag Berlin Heidelberg, pp. 1.*
Drummond, "Discriminative vs. Generative Classifiers for Cost Sensitive Learning," Proceedings of the 19th international conference on Advances in Artificial Intelligence: Canadian Society for Computational Studies of Intelligence, 2006, pp. 479-490.
Elkan and Noto, "Learning Classifiers from Only Positive and Unlabeled Data," KDD '08 Proceedings of the 14th ACM SIGKDD international conference on Knowledge discovery and data mining, Aug. 24-27, 2008, pp. 213-220.

(Continued)

*Primary Examiner* — David Vincent
(74) *Attorney, Agent, or Firm* — Fish & Richardson P.C.

(57) ABSTRACT

Described is a machine learning system for binary classifications. The system improves interpolation schemes used in isotonic regressions by providing a continuous function that also is monotonic. The system outputs a probability estimating function on a signal space that is both monotonic and varies continuously with the input signals. More specifically, described is an interpolation function that is continuous and piecewise linear on Delaunay simplices. Accordingly, the resulting probability estimation function may more accurately match actual probabilities especially when training data is sparse.

10 Claims, 3 Drawing Sheets

(56) References Cited

OTHER PUBLICATIONS

Lin and Li, "Large-Margin Thresholded Ensembles for Ordinal Regression: Theory and Practice," ALT'06 Proceedings of the 17th international conference on Algorithmic Learning Theory, 2006, pp. 319-333.

Noumir et al., "Multi-Class Least Squares Classification at Binary-Classification Complexity," 2011 IEEE Statistical Signal Processing Workshop (SSP), Jun. 28-30, 2011, pp. 277-280.

* cited by examiner

INTERPOLATING ISOTONIC REGRESSION FOR BINARY CLASSIFICATION OF SPAM, EXPLICIT MATERIAL OR MALWARE USING INTERPOLATION BASED ON A DELAUNAY TRIANGULATION

BACKGROUND

Systems that analyze online content such as webpages, media, and documents may employ binary classification schemes. In order to perform content classification, systems may employ machine learning techniques. For example, a machine learning system may be trained on email messages to learn to distinguish between spam and non-spam messages. In response to this "learning," the system may be used to classify new email messages by flagging those that may be considered spam. When classifying content, the learning techniques employed by systems often utilize a form of regression analysis to analyze training data. Typical regression analysis algorithms, however, may provide less than optimal results especially in instances where training data is sparse.

BRIEF SUMMARY

In an implementation, described is a computer-implemented method for interpolating isotonic regression in a binary classifier system. The method may include receiving a set of training examples for content items, each training example including a positive or negative label for a classification and a value for each of D attributes of the content items, wherein the values are provided as D-dimensional coordinates. These attributes may include a text attribute or a non-text attribute. The method may include determining an interpolation function based on a Delaunay triangulation of coordinates in the received training set, wherein the determined function satisfies monotonicity constraints and includes maximizing a likelihood of an observation subject to the monotonicity constraints. The method may also include receiving the observation for a content item, the observation including D-dimensional coordinates, and determining a probability that the observation is positive for the classification based on the determined interpolation function. For example, the classification may include spam, explicit material, and/or malware. The monotonicity constraints may be based on a matrix of a coordinate representation of a linear map from barycentric coordinates to projective feature space coordinates. In addition, the maximized likelihood of the observation subject to the monotonicity constraints may be based on the interpolation function linearly interpolating over simplices.

In an implementation, described is a system for interpolating isotonic regression in a binary classifier system. The system may include a processor configured to receive a set of training examples for content items, each training example including a positive or negative label for a classification and a value for each of D attributes of the content items, wherein the values are provided as D-dimensional coordinates. The processor may be configured to determine an interpolation function based on a Delaunay triangulation of coordinates in the received training set, wherein the determined function satisfies monotonicity constraints and includes maximizing a likelihood of an observation subject to the monotonicity constraints. The processor may also be configured to receive the observation for a content item, the observation including D-dimensional coordinates, and determine a probability that the observation is positive for the classification based on the determined interpolation function.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

Described is a system and method for interpolating an isotonic regression for binary classification. As described, a system may classify various forms of content using a machine learning approach. Current systems often employ a multivariate monotonic regression in machine learning systems when training a binary classifier (e.g. 0/1 classification). In particular, monotonic regression is often used in situations where the probability for an item to be classified as positive for a trait (e.g. "1") does not decrease if the values of an input signal increases. One drawback of this approach, however, is that monotonic regression typically only gives well-defined probabilities for items with signal combinations represented in the training set. Accordingly, in order to address points in-between the training set points, the system must often employ some form of interpolation. Interpolation schemes typically used in monotonic regression, however, usually either violate monotonicity themselves and/or violate continuity.

The present disclosure may overcome these limitations in typical interpolations schemes by providing a continuous function that also is monotonic. Described is a method that outputs a probability estimating function on a signal space that is both monotonic and varies continuously with the input signals. More specifically, described is an interpolation function that is continuous and piecewise linear on Delaunay simplices. Accordingly, the resulting probability estimation function may more accurately match actual probabilities. For example, slight changes in a signal may result in a relatively slight change in probability predictions, as opposed to sudden relatively large changes that may result from conventional interpolation techniques. Accordingly, the system described herein may provide improved results over traditional isotonic regression techniques particular in instances where the training set is sparse.

In order to provide an interpolation function, techniques disclosed herein may modify the monotonic regression problem such that the monotonicity constraints are not provided as constraints on probability estimates at pairs of training set points, but as constraints on partial derivatives of the interpolation function (which is a member of a finite-dimensional function space). In an implementation, the set of candidate interpolation functions may be piecewise linear on Delaunay simplices defined by training set points. For example, this technique may borrow from interpolation over unstructured mesh techniques (e.g. techniques applied in mechanical engineering contexts) to map the per-simplex monotonicity constraints on an output function to linear inequalities in the function values at mesh vertices. This defines a convex optimization problem for which a feasible point may be determined, and thus, may be solved using known convex optimization techniques.

Figure 1:
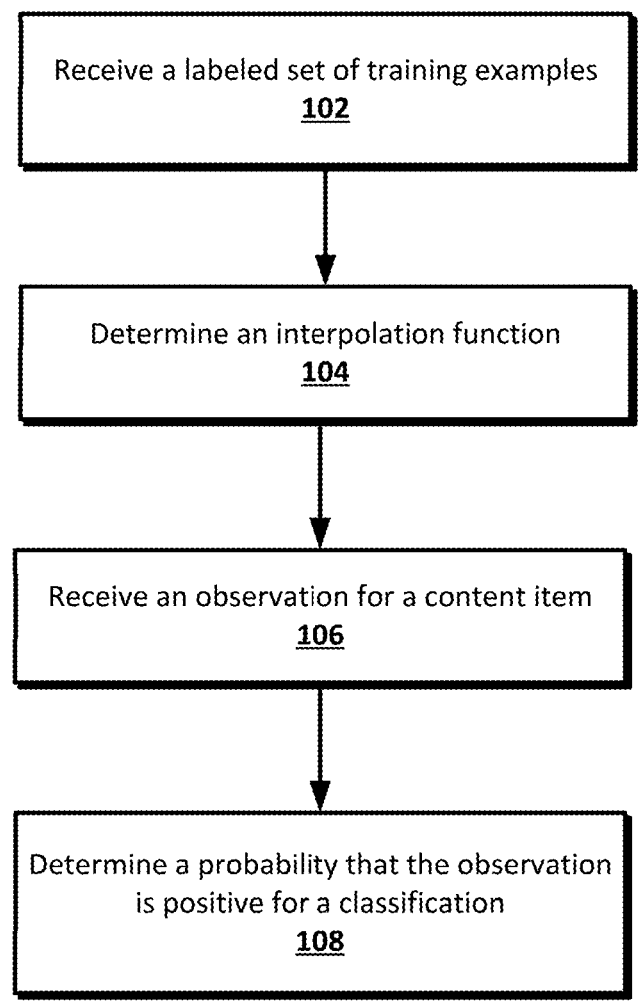
FIG. 1 shows a flow diagram of determining the probability that a content item is positive for a trait according to an implementation of the disclosed subject matter.

FIG. 1 shows a flow diagram of a process for determining the probability that a content item is positive for a trait according to an implementation of the disclosed subject matter. In 102, the system may receive a set of training examples for content items. In an implementation, each training example may include a positive or negative label for a classification. For example, a positive (e.g. 1) or negative (e.g. 0) label may indicate a classification for a content item. These classifications may include spam, explicit material, malicious material or malware, and other types of classifiable characteristics. Explicit material, for example, may include material including nudity, sexuality, particular language, violence, etc. For example, explicit material may be based on certain parental control settings and/or filters. Malware, for example, may include computer viruses, ransomware, worms, trojan horses, rootkits, keyloggers, dialers, spyware, adware, rogue security software and/or other malicious programs. In technical terms, malware may also be known as a "computer contaminant," as defined, for example, in the legal codes of several U.S. states.

The training example may include values for each of a D number of attributes of the content items. For example, attributes of a content item may include text and non-text (e.g. images) components. Accordingly, each of these attributes may be assigned a value (or input value). For instance, a non-text attribute (e.g. image) with the highest degree of explicit material may be assigned a value of 1 and a text attribute with the lowest degree of explicit material may be assigned a value of 0. These values may be provided to the system as D-dimensional coordinates. For example, values for a content item with two attributes as described above (text and non-text) may be represented by the coordinates (1, 0). Similarly, a content item with a moderate amount of explicit material in both images and text may be represented by the coordinates (0.5, 0.5). In addition to coordinates, these values may be represented by a vector in a D-dimensional feature space.

In 104, the system may determine an interpolation function. As further described herein, the function may be based on a Delaunay triangulation of coordinates in the received training set. In addition, the determined function may satisfy monotonicity constraints and include maximizing a likelihood of an observation, wherein the observation is subject to the monotonicity constraints.

In 106, the system may receive an observation of a content item. As described above, an observed content item may include values for a number of attributes, D, of the content items. For example, an observation including values for explicit images and text may be received. In 108, the system may determine a probability that the observation is positive for the classification based on the determined interpolation function. For example, the function may output the probability that the observed content item may be classified as containing explicit material.

When determining an interpolation function, a maximum likelihood regression problem may be modified such that a function F on a feature space satisfies the following properties:

1) F may be defined and continuous on the convex hull of all points $\vec{X}_i$ in the training set.

2) F may be differentiable everywhere except on a set of measure zero, and the partial derivatives may respect monotonicity constraints $$\frac{\partial F}{\partial x} \geq 0$$

wherever defined.

3) F may maximize a likelihood of the observations subject to the monotonicity constraints.

4) If the $\vec{X}_i$ are in a general position and the simplex S is the convex hull of a subset of D+1 points $X_{Si}$, i=1 . . . D+1 such that none of the $X_i$ lies strictly within the circumsphere of S, then the gradient $\nabla F$ may be constant on the interior of S.

Accordingly, property 4 means that the particular gradient of F may have a finite number of different values. This may be regarded as constraining interpolation to a plausible higher-dimensional generalization of 1–D linear interpolation. A linear interpolation in D dimensions may take a weighted average of D+1 support points. In one dimension, the constraint to only consider sets of D+1=2 support points that do not contain any support point in the interior of their convex hull is sufficient to uniquely define the underlying partitioning; however, a stronger condition is needed in higher dimensions. The 'no other points inside the circumsphere' condition may avoid simplices with very uneven extensions, but requires a notion of Euclidean distance on a feature space. This property may be satisfied by generalized higher-dimensional Delaunay triangulations. Accordingly, the function F may be obtained as follows:

1) Computation of the Delaunay triangulation of the training set in a feature space.

2) For D-dimensional simplex S obtained in the step 1, the function F has to satisfy D constraints $(\partial/\partial x_i) F_{|S} \geq 0$. The may be translated to D linear inequalities in the value of F at the vertices of S.

3) Accordingly, since the likelihood function is convex and a feasible point may be given by $F_0(\vec{X}_i)=0.25+(0.5/D) \Sigma_j q_j((X_1)_j)$, where i∈1 . . . N, j∈1 . . . D, and $q_j$ is the quantile function for the j-th feature, the resulting convex optimization problem may be solved with standard convex optimization techniques.

Barycentric coordinates may be used to obtain the linear inequalities on the $F(\vec{X}_i)$ required in step 2 above. For a given D-dimensional simplex S with vertices $\vec{X}_S\alpha$, a∈1 . . . (D+1), barycentric coordinates of a point X are a (D+1)-dimensional vector $(L_1, L_2, \ldots L_{D+1})^T$ s.t. $L_\alpha$ is the volume ratio $L_\alpha$=Vol(Simplex $S$ with α-th vertex replaced by $\vec{X}$)/Vol(Simplex $S$).

Figure 2:
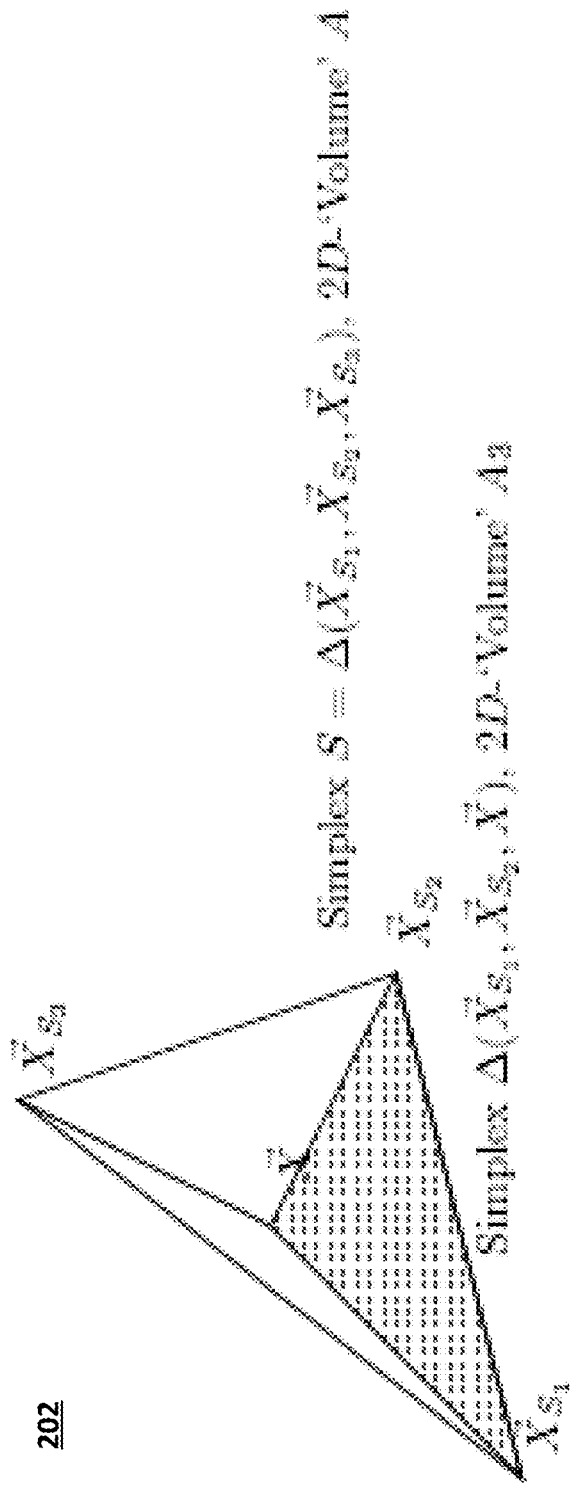
FIG. 2 shows a simplex according to an implementation of the disclosed subject matter.

FIG. 2 shows a simplex according to an implementation of the disclosed subject matter. In two dimensions, barycentric 'coordinates' $L_1, L_2, L_3$ of point $\vec{X}$ for simplex S (as shown as 202) provide the area fractions $L_1=A_1/A$, $L_2=A_2/A$, $L_3=A_3/A$, where A is the area of the simplex (triangle), and $A_i$ is the area of the simplex obtained by replacing the i-th vertex with $\vec{X}$. The $L_j$ are invariant under affine transformations of the plane and sum to 1 and extend outside S if volume orientations are taken into account. Accordingly, barycentric coordinates provide a symmetric parameterization w.r.t. permutation of D+1 vertices in D dimensions at the expense of having one linear constraint, $\Sigma\, L_i = 1$.

In certain situations, it may be useful to introduce projective coordinates on a feature space by adding a (D+1)-th coordinate that is set to 1 for every feature vector $X_i$ in the training set, $(X^*_i)_j := \{(X_i)_j \text{ if } j \leq D,\, 1 \text{ if } j = D+1, i \text{ in } 1 \ldots N\}.$ Then, the matrix $M^{(S)}$ defined by $M_{ji}^{(S)} := (X^*_{Si})_j$ maps barycentric coordinates to projective feature space coordinates. For example, $(L_1, L_2, \ldots L_{D+1})$ are barycentric coordinates of point $\vec{P}$ w.r.t. simplex S, then $\Sigma_j L_j = 1$ and $P^*_j = \Sigma_i M_{ji}^{(S)} L_i$ are extended feature space coordinates of $\vec{P}$.

The inverse of the matrix $M^{(S)}$ maps projective feature space coordinates to barycentric coordinates and hence allows the re-write of $\partial/\partial x_i F(\vec{X}) \geq 0$ on S in terms of $\partial/\partial L_i$ on S. Accordingly, F on S may be expressed in barycentric coordinates as $F(\vec{P}) = L_1 F(S_1) + L_2 F(S_2) + \ldots + L_{D+1} F(S_{D+1})$, and each monotonicity constraint may give a linear inequality in the $F(S_i)$. Explicitly, $$\left(\frac{\partial}{\partial xi}\right)F_{|S} \geq 0 = \sum_j \left(\frac{\partial Lj}{\partial xi}\right)\frac{\partial}{\partial Lj}F_{|S} \geq 0$$

$$= \sum_j (M^{(S)})^{-1}_{ji} F(\vec{X}_j) \geq 0 \ (i \in 1 \ldots D).$$

Accordingly, the solution to the problem described above may be defined as follows: given a set of N labeled observations $(Y_i, X_i)$ where $Y_i$ are binary labels $\in \{0;\, 1\}$ and $\vec{X}_i$ are points in a D-dimensional feature space (and may be normalized by mapping to quantiles), first determine a (D-dimensional simplicial) Delaunay "triangulation" T of $\{\vec{X}_i\}$ and then maximize likelihood $L(P_1, \ldots P_N) = -\Sigma(Y_i \log(P_i) + (1-Y_i) \log(1-P_i))$ subject to the linear constraints $\Sigma_j (M)^{(S)}_{ji}^{-1} P_j \geq 0$ (i∈1 ... D, S∈T), where the matrix $M^{(S)}$ is the coordinate representation of the linear map from barycentric coordinates on S to projective feature space coordinates. In this sum, the value of P log P in this sum is taken as 0 if P=0. Accordingly, linear interpolation over simplices may then give the desired likelihood-maximizing interpolation function on signal space that satisfies monotonicity constraints.

Figure 3:
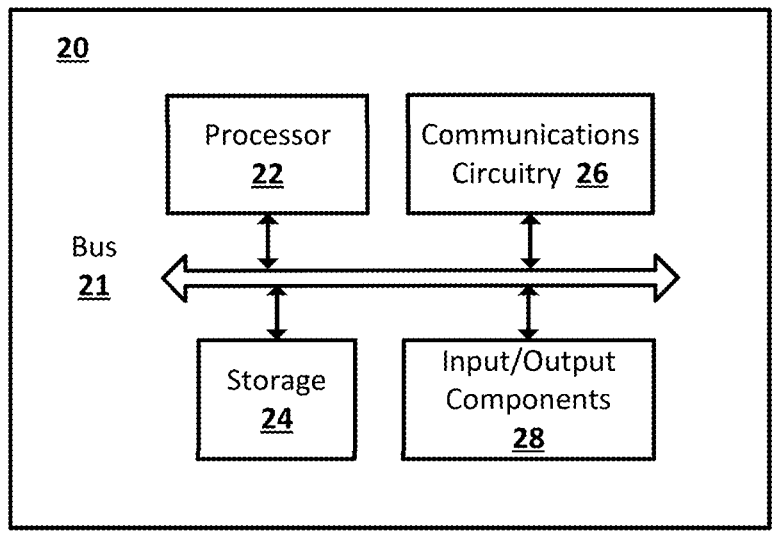
FIG. 3 shows a block diagram of a computer system according to an implementation of the disclosed subject matter.

FIG. 3 shows a block diagram of a computer system according to an implementation of the disclosed subject matter. Implementations of the disclosed subject matter may be used with a variety of component and network architectures. The computer 20 may include a bus 21 which interconnects major components of the computer 20, such as a processor 22, a storage 24, communications circuitry 26, and input/output components 28. The processor 22 may be any suitable programmable control device and may control the operation of one or more processes as discussed herein and other processes performed by the computer 20. The computer 20 may host one or more applications configured to manage services that may be associated with a user account. The computer may maintain information related to a user account including account details, preferences, user history, etc.

The storage 24 may be integral with the computer 20 or may be separate and accessed through an interface. The storage 24 may store content (e.g. video, music, photos, applications, and documents etc.), software (e.g., for implementing various functions on computer 20), and other data. The storage 24 may include a suitable storage medium, such as one or more hard-drives, solid state drives, flash drives, and the like.

The input/output components 28 may include outputs components and/or interfaces for a display that provides visual output. The input/output component may also include input components and/or interfaces for user input devices that allow a user to interact with the computer 20. For example, the user input devices may include a keyboard, a keypad, a mouse, touchpad, a touch screen, and the like.

The communications circuitry 26 may include one or more interfaces to allow the computer 20 to communicate with other computers 20, devices 10 and/or databases 29 via one or more local, wide-area, or other networks, as shown in FIG. 2. In addition, various high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor to control such communications intensive tasks such as packet switching, content management, and content delivery.

Figure 4:
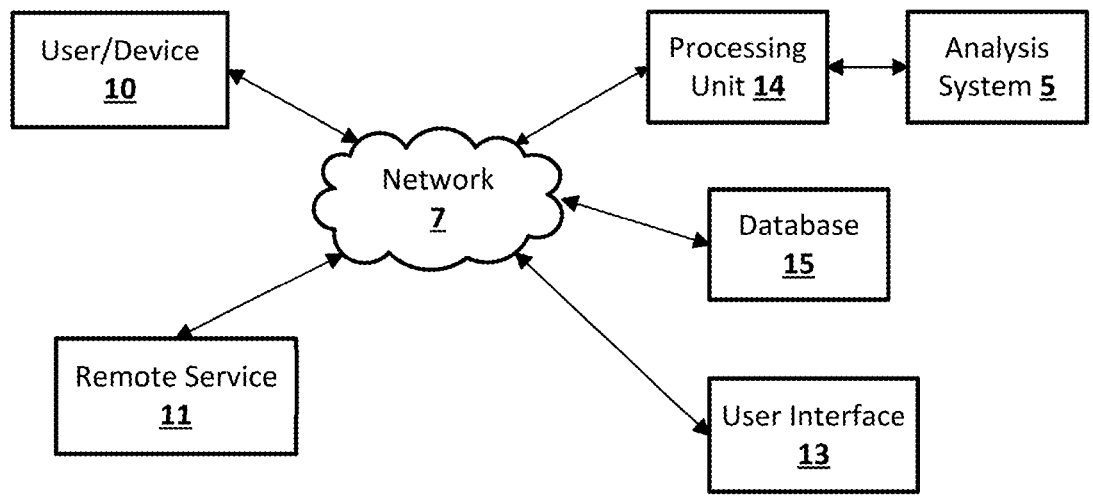
FIG. 4 shows an example network arrangement according to an implementation of the disclosed subject matter.

FIG. 4 shows an example network arrangement according to an implementation of the disclosed subject matter. One or more clients 10, 11, such as local computers, smart phones, tablet computing devices, remote services, and the like may connect to other devices via one or more networks 7. The network 7 may be a local network, wide-area network (including the Internet), or any other suitable communication network or networks, and may be implemented on any suitable platform including wired and/or wireless networks. The network 7 may be part of a public and/or a private network any may also include one or more gateways, which facilitate the transfer of data between devices using different protocols. Further, the network 7 may include secure links and/or unsecure links. Additionally, the network 7 may include network infrastructure provided by multiple parties, such as a host network and one or more partner networks (e.g. roaming partners).

The clients 10, 11 may communicate with one or more computer systems, such as processing units 14, databases 15, and user interface systems 13. In some cases, clients 10, 11 may communicate with a user interface system 13, which may provide access to one or more other systems such as a database 15, a processing unit 14, or the like. For example, the user interface 13 may be a user-accessible web page that provides data from one or more other computer systems. The user interface 13 may provide different interfaces to different clients, such as where a human-readable web page is provided to web browser clients 10, and a computer-readable API or other interface is provided to remote service clients 11. The user interface 13, database 15, and processing units 14 may be part of an integral system, or may include multiple computer systems communicating via a private network, the Internet, or any other suitable network. Processing units 14 may be, for example, part of a distributed system such as a cloud-based computing system, search engine, content delivery system, or the like, which may also include or communicate with a database 15 and/or user interface 13. In some arrangements, an analysis system 5 may provide back-end processing, such as where stored or acquired data is pre-processed by the analysis system 5 before delivery to the processing unit 14, database 15, and/or user interface 13. For example, a machine learning system may be implemented on the analysis system 5 and may provide various prediction models, data analysis, or the like to one or more other systems 13, 14, 15.

In situations in which the implementations of the disclosed subject matter collect and/or use personal information about users (e.g. a user history, geographic location, or other information associated with a user), the system may provide users with the ability to control and/or set preferences related to the collection of such data. In addition, certain information may be treated in one or more ways before it is stored or used, so that personally identifiable information is removed. For example, a user's identity may be treated so that no personally identifiable information can be determined for the user, or a user's geographic location associated with an instructional course may be generalized where location information is obtained (e.g. ZIP code), so that a particular location of a user cannot be determined. Thus, the user may have control over how user history information may be collected.

Various implementations may include or be embodied in the form of computer-implemented process and an apparatus for practicing that process. Implementations may also be embodied in the form of a non-transitory computer-readable storage and/or memory containing instructions, wherein, when the instructions are loaded into and executed by a computer (or processor), the computer becomes an apparatus for practicing implementations of the disclosed subject matter.

The flow diagrams described herein are included as examples. There may be variations to these diagrams or the steps (or operations) described therein without departing from the implementations described. For instance, the steps may be performed in parallel, simultaneously, a differing order, or steps may be added, deleted, or modified. Similarly, the block diagrams described herein are included as examples. These configurations are not exhaustive of all the components and there may be variations to these diagrams. Other arrangements and components may be used without departing from the implementations described herein. For instance, components may be added, omitted, and may interact in various ways known to an ordinary person skilled in the art.

References to "one implementation," "an implementation," "an example implementation," and the like, indicate that the implementation described may include a particular step, feature, structure, or characteristic, but every implementation may not necessarily include the particular step, feature, structure, or characteristic. Moreover, such phrases are not necessarily referring to the same implementation. Further, when a particular step, feature, structure, or characteristic is described in connection with an implementation, such step, feature, structure, or characteristic may be included in other implementations whether or not explicitly described. The term "substantially" may be used herein in association with a claim recitation and may be interpreted as "as nearly as practicable," "within technical limitations," and the like.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A computer-implemented method for interpolating isotonic regression in a binary classifier system, comprising:
   receiving a set of training examples for content items, each training example including a positive or negative label for a classification and a respective value for each of D attributes of the content items, wherein the values are provided as D-dimensional coordinates;
   determining an interpolation function based on a Delaunay triangulation of coordinates in the received set of training examples, wherein the determined function satisfies monotonicity constraints and includes maximizing a likelihood of an observation subject to the monotonicity constraints;
   receiving a first observation for a first content item, the first observation including D-dimensional coordinates; and
   determining a probability that the first observation is positive for the classification based on the determined interpolation function, wherein the classification is one of spam, explicit material, and malware.

2. The method of claim 1, wherein the attributes include at least one of a text attribute and a non-text attribute.

3. The method of claim 1, wherein the coordinates are values between 0 and 1.

4. The method of claim 1, wherein the monotonicity constraints are based on a matrix of a coordinate representation of a linear map from barycentric coordinates to projective feature space coordinates.

5. The method of claim 1, wherein the maximized likelihood of the observation subject to the monotonicity constraints is based on the interpolation function linearly interpolating over simplices.

6. A system for interpolating isotonic regression in a binary classifier system, comprising:
   one or more computers and one or more storage devices storing instructions that are operable, when executed by the one or more computers, to cause the one or more computers to perform operations comprising:
   receiving a set of training examples for content items, each training example including a positive or negative label for a classification and a respective value for each of D attributes of the content items, wherein the values are provided as D-dimensional coordinates;
   determining an interpolation function based on a Delaunay triangulation of coordinates in the received set of training examples, wherein the determined function satisfies monotonicity constraints and includes maximizing a likelihood of an observation subject to the monotonicity constraints;
   receiving the observation for a content item, the observation including D-dimensional coordinates; and
   determining a probability that the observation is positive for the classification based on the determined interpolation function, wherein the classification is one of spam, explicit material, and malware.

7. The system of claim 6, wherein the attributes include at least one of a text attribute and a non-text attribute.

8. The system of claim 6, wherein the coordinates are values between 0 and 1.

9. The system of claim 6, wherein the monotonicity constraints are based on a matrix of a coordinate representation of a linear map from barycentric coordinates to projective feature space coordinates.

10. The system of claim 6, wherein the maximized likelihood of the observation subject to the monotonicity constraints is based on the interpolation function linearly interpolating over simplices.

* * * * *